United States Patent
Aoki

(10) Patent No.: US 8,131,451 B2
(45) Date of Patent: Mar. 6, 2012

(54) AIR-FUEL RATIO SENSOR AND CONTROL APPARATUS FOR INTERNAL COMBUSTION ENGINE

(75) Inventor: Keiichiro Aoki, Numazu (JP)

(73) Assignee: Toyota Jidosha Kabushiki Kaisha, Toyota-shi (JP)

(*) Notice: Subject to any disclaimer, the term of this patent is extended or adjusted under 35 U.S.C. 154(b) by 126 days.

(21) Appl. No.: 12/744,942

(22) PCT Filed: Nov. 26, 2008

(86) PCT No.: PCT/JP2008/071395
§ 371 (c)(1),
(2), (4) Date: May 27, 2010

(87) PCT Pub. No.: WO2009/069624
PCT Pub. Date: Jun. 4, 2009

(65) Prior Publication Data
US 2010/0300418 A1    Dec. 2, 2010

(30) Foreign Application Priority Data
Nov. 27, 2007    (JP) .................................. 2007-305443

(51) Int. Cl.
*B60T 7/12* (2006.01)
(52) U.S. Cl. ............. 701/109; 123/688; 60/274; 60/276
(58) Field of Classification Search .................. 701/109; 123/688, 691, 703; 60/274, 275, 276, 277, 60/285, 289
See application file for complete search history.

(56) References Cited

U.S. PATENT DOCUMENTS

| | | | | |
|---|---|---|---|---|
| 5,743,085 | A * | 4/1998 | Takaku et al. | 60/276 |
| 5,921,078 | A * | 7/1999 | Takaku et al. | 60/277 |
| 6,089,016 | A * | 7/2000 | Takaku | 60/277 |
| 6,210,641 | B1 * | 4/2001 | Yamada et al. | 422/94 |
| 2003/0061862 | A1 | 4/2003 | Kondo et al. | |
| 2007/0017210 | A1 | 1/2007 | Hirata et al. | |
| 2009/0037079 | A1 | 2/2009 | Suzuki et al. | |
| 2009/0056686 | A1 | 3/2009 | Suzuki | |
| 2009/0089011 | A1 * | 4/2009 | Iwazaki et al. | 702/183 |

FOREIGN PATENT DOCUMENTS

| | | |
|---|---|---|
| JP | 11 237361 | 8/1999 |
| JP | 2003 107047 | 4/2003 |
| JP | 2003 202316 | 7/2003 |

(Continued)

*Primary Examiner* — John Kwon
(74) *Attorney, Agent, or Firm* — Oblon, Spivak, McClelland, Maier & Neustadt, L.L.P.

(57) ABSTRACT

There is provided an air-fuel ratio sensor with which an improvement in the accuracy in detecting the air-fuel ratio of detection target gas and an improvement in the response characteristics can both be achieved. The sensor includes a sensor element that outputs an output signal indicative of the air-fuel ratio of a detection target gas, a pair of electrodes including a detection target gas side electrode to which the detection target gas is introduced and an atmosphere side electrode exposed to the atmosphere, which are arranged in such a way as to sandwich the sensor element, a diffusion-controlling layer that is disposed on the sensor element in such a way as to cover the detection target gas side electrode and introduces the detection target gas from an entrance portion through which the detection target gas flows in to the detection target gas side electrode, and a catalyst layer provided on a part of the entrance portion.

4 Claims, 7 Drawing Sheets

FOREIGN PATENT DOCUMENTS

| | | |
|---|---|---|
| JP | 2004 316498 | 11/2004 |
| JP | 2006 52684 | 2/2006 |
| JP | 2006 322389 | 11/2006 |
| JP | 2006 337205 | 12/2006 |
| JP | 2007 154840 | 6/2007 |
| JP | 2007 155605 | 6/2007 |
| JP | 2007 211609 | 8/2007 |

* cited by examiner

US 8,131,451 B2

AIR-FUEL RATIO SENSOR AND CONTROL APPARATUS FOR INTERNAL COMBUSTION ENGINE

This application is the national phase application under 35 U.S.C. §371 of PCT international application No. PCT/JP2008/071395 filed on 26 Nov. 2008, which claims priority to Japanese patent application No. 2007-305443 filed on 27 Nov. 2007, the contents of which are incorporated herein by reference.

TECHNICAL FIELD

The present invention relates to an air-fuel ratio sensor and a control apparatus for an internal combustion engine.

BACKGROUND ART

An air-fuel ratio sensor that senses the air-fuel ratio of the exhaust gas is provided in the exhaust system of an internal combustion engine in some cases in order to control the air-fuel ratio of the internal combustion engine. As an air-fuel ratio sensor, a limiting current type air-fuel ratio sensor has been developed as described in Patent Document 1. This limiting current type air-fuel ratio sensor comprises a sensor element made of an oxygen ion conductive solid electrolyte such as zirconia, a pair of platinum electrodes provided on two sides of the sensor element, and a porous diffusion-controlling layer (which is also referred to as a "diffusion resistance layer" in some cases) provided on the element in such a way as to cover one of the electrodes. The diffusion-controlling layer controls or limits the diffusion of the exhaust gas toward the sensor element.

In such a limiting current type air-fuel ratio sensor, when the exhaust gas having passed through the diffusion-controlling layer comes in contact with one electrode while a predetermined voltage is applied between the electrodes, oxygen ions are pumped between the electrodes through the sensor element, whereby a current flows between the electrodes. In connection with this, since the diffusion of the exhaust gas toward one electrode is limited by the diffusion-controlling layer, there is a region in which the current saturates to a constant value in spite of increases in the applied voltage. This current value (or the limit current value) has a characteristic proportional to the oxygen concentration and the air-fuel ratio of the exhaust gas, and therefore the air-fuel ratio can be determined by measuring the limit current value.

The reason why a constant current of the limit current value correlating with the air-fuel ratio of the exhaust gas flows between the electrodes when the predetermined voltage is applied between the electrodes is that the current is diffusion-limited as the exhaust gas passes through the diffusion-controlling layer. However, since the molecular mass of the hydrogen ($H_2$) component contained in the exhaust gas is smaller than those of the other components such as oxygen ($O_2$), the hydrogen component passes through the diffusion-controlling layer at a higher diffusion rate characteristically. In consequence, if the amount of $H_2$, which serves as a reducing agent, reaching one electrode is larger than that of $O_2$, which serves as an oxidizing agent, the reducing agent becomes overabundant in the vicinity of this electrode, whereby an air-fuel ratio that is erroneously richer than its actual value may be obtained as the measurement result.

This is addressed by the technology disclosed in Patent Document 1 in which the surface of the diffusion-controlling layer is covered with a catalyst layer having an oxidizing ability to oxidize $H_2$ contained in the exhaust gas before the exhaust gas passes through the diffusion-controlling layer, whereby the accuracy in measuring the air-fuel ratio is improved.

Patent Document 2 also discloses a technology in which a catalyst layer with which at least one electrode exposed to the exhaust gas is covered is provided, and a mask layer through which the exhaust gas cannot pass is provided on a portion on which the catalyst layer is not provided.

Patent Document 1: Japanese Patent Application Laid-Open No. 11-237361
Patent Document 2: Japanese Patent Application Laid-Open No. 2003-202316
Patent Document 3: Japanese Patent Application Laid-Open No. 2004-316498
Patent Document 4: Japanese Patent Application Laid-Open No. 2006-337205

DISCLOSURE OF THE INVENTION

Problem to be Solved by the Invention

However, in the air-fuel ratio sensor provided with a catalyst layer as is the case with the above-described prior art, if the entire amount of the exhaust gas for which detection of air-fuel ratio is to be performed is caused to pass through the catalyst layer, a long time is taken by the reaction in the catalyst layer, and the response characteristics in detecting the air-fuel ratio can be deteriorated.

The present invention has been made in view of the above-described prior arts, and an object thereof is to provide an air-fuel ratio sensor with which an improvement in the accuracy in detecting the air-fuel ratio of detection target gas and an improvement in the response characteristics can both be achieved.

Means for Solving the Problem

To achieve the above object, the air-fuel ratio sensor according to the present invention adopts the following configurations. Specifically, it is characterized by comprising a sensor element that outputs an output signal indicative of the air-fuel ratio of a detection target gas, a pair of electrodes including a detection target gas side electrode to which said detection target gas is introduced and an atmosphere side electrode exposed to the atmosphere, which are arranged in such a way as to sandwich said sensor element, a diffusion-controlling layer that is disposed on said sensor element in such a way as to cover said detection target gas side electrode and introduces said detection target gas from an entrance portion through which said detection target gas flows in to said detection target gas side electrode, and a catalyst layer provided on a part of said entrance portion.

The diffusion-controlling layer according to the present invention has the entrance portion through which the detection target gas (e.g. exhaust gas) flows in, and the detection target gas flows into the diffusion-controlling layer through the entrance portion. In other words, the entrance portion is provided on at least a part of the surface of the diffusion-controlling layer and exposed to the detection target gas. The detection target gas having flown into the diffusion-controlling layer diffuses in the interior of the diffusion-controlling layer and is delivered to the detection target gas side electrode. The diffusion-controlling layer according to the present invention has the function of controlling or limiting the diffusion of the detection target gas. The diffusion-controlling layer may be composed, for example, of a poromeric material which is porous but dense to the extent that various components in the detection target gas can diffuse at an appropriate diffusion rate.

The detection target gas diffusing in the interior of the diffusion-controlling layer contains reducing agents such as CO, $H_2$, and HC and oxidizing agents such as $O_2$ and NOx. These components react with each other while they travel to the surface of the detection target gas side electrode and after reaching the detection target gas side electrode, until an equilibrium is reached. In the case where the air-fuel ratio of the detection target gas is equal to the theoretical air-fuel ratio (or stoichiometric air-fuel ratio), the oxidizing agents and the reducing agents both disappear. On the other hand, in the case where the air-fuel ratio is rich, the reducing agents will remain, and in the case where the air-fuel ratio is lean, the oxidizing agents will remain.

The sensor element outputs an output signal indicative of the air-fuel ratio of the detection target gas. The sensor element may be made of an oxygen ion conductive solid electrolyte. If this is the case, since oxygen ions move in accordance with the difference in the oxygen concentration between two electrodes that are disposed in such a way as to sandwich the sensor element, or the detection target gas side electrode and the atmosphere side electrode, the output signal indicative of the air-fuel ratio of the detection target gas can be output by outputting a sensor current caused by the movement of the oxygen ions.

Here, the sensor current will be described more specifically. In the case where there remain oxidizing agents in the detection target gas that has come to the surface of the detection target gas side electrode, $O_2$ is pumped from the detection target gas side electrode toward the atmosphere side electrode, whereby a sensor current flows between the electrodes. On the other hand, in the case where there remain reducing agents in the detection target gas that has come to the detection target gas side electrode, $O_2$ that is needed to oxidize the reducing agents is pumped from the atmosphere side electrode toward the detection target gas side electrode, whereby a sensor current flows between the electrodes. Since the sensor current value at that time shows a characteristic proportional to the air-fuel ratio of the detection target gas, the air-fuel ratio of the detection target gas can be detected or determined by sensing this sensor current value.

$H_2$ has, characteristically, a higher diffusion rate as compared to the other components in the detection target gas, in particular $O_2$. Therefore, the ratio of $H_2$ and $O_2$ contained in the detection target gas may change in some cases as the gas diffuses in the interior of the diffusion-controlling layer. Specifically, a larger quantity of $H_2$, which has a higher diffusion rate as compared to $O_2$, will reach the detection target gas side electrode. Since $H_2$ is a reducing agent, the aforementioned sensor current value can be detected as a value shifted to richer air-fuel ratios than the true value.

According to the present invention, the catalyst layer is provided on a part of the entrance portion of the diffusion-controlling layer. The catalyst layer according to the present invention has the function of promoting the oxidation reaction of the $H_2$ component. A catalyst component such as platinum or rhodium may be supported, for example, on a porous layer made of a alumina or the like serving as a catalyst support. The catalyst layer may be able to oxidize components other than $H_2$.

The part of the entrance portion of the diffusion-controlling layer on which the catalyst layer is provided will be referred to as the entrance portion with catalyst layer, and the part on which the catalyst layer is not provided will be referred to as the entrance portion without catalyst layer.

Since the most part of $H_2$ in the detection target gas flowing into the diffusion-controlling layer through the entrance portion with catalyst layer is oxidized while the gas passes through the catalyst layer, the detection target gas in an equilibrium state can be introduced to the detection target gas side electrode. Consequently, the detection target gas having an air-fuel ratio substantially equal to the air-fuel ratio before the entrance into the diffusion-controlling layer through the entrance portion with catalyst layer can be delivered to the surface of the detection target gas side electrode. This assures the accuracy of detection of the air-fuel ratio by the air-fuel ratio sensor.

In the air-fuel ratio sensor, an improvement in the accuracy of air-fuel ratio detection and an improvement in the response characteristics are both desired to be achieved. In other words, in order to detect the air-fuel ratio of the detection target gas on a real-time basis, it is required to make the time taken to detect the air-fuel ratio as short as possible. Detection of the air-fuel ratio of the detection target gas flowing into the diffusion-controlling layer through the catalyst layer in the entrance portion with catalyst layer may sometimes delay due to the reaction time in the catalyst layer.

This is addressed by the present invention, according to which the detection target gas is caused to flow into the diffusion-controlling layer also through the entrance portion without catalyst layer on which the catalyst layer is not provided, whereby the detection target gas can be delivered to the detection target gas side electrode quickly. This enables a reduction in the time taken to detect the air-fuel ratio of the detection target gas. That is to say, according to the present invention, the detection target gas is caused to flow into the diffusion-controlling layer through the entrance portion with catalyst layer and the entrance portion without catalyst layer, and the gases join together in the vicinity of the detection target gas side electrode, whereby improvement in the accuracy of air-fuel ratio detection and improvement in the response characteristics can both be achieved.

In the present invention, the area of the entrance portion with catalyst layer and the area of the entrance portion without catalyst layer may be equal to or different from each other. In other words, the ratio of the area of the entrance portion with catalyst layer and the area of the entrance portion without catalyst layer may be changed fitly. It is preferred that the ratio of the areas of the entrance portion with catalyst layer and the entrance portion without catalyst layer be changed in accordance with the balance between the degree of accuracy of air-fuel ratio detection that the air-fuel ratio sensor according to the present invention is required to provide and the response performance thereof. More specifically, if the accuracy of detection of the air-fuel ratio is to be enhanced, the proportion of the entrance portion with catalyst layer may be made larger, and if the response performance is to be enhanced, the proportion of the entrance portion without catalyst layer may be made larger.

In the present invention, the term "air-fuel ratio sensor" collectively denotes a unit that can output a physical quantity indicative of the oxygen concentration in the detection target gas to detect or measure the air-fuel ratio in the internal combustion engine, and the air-fuel ratio sensor may be a linear air-fuel ratio sensor, an $O_2$ sensor, or the like. The physical quantity indicative of the oxygen concentration may be a current value or a voltage value.

Here, a description will be made of a case where the above-described air-fuel ratio sensor is used in detecting the air-fuel ratio of the exhaust gas discharged from a multi-cylinder internal combustion engine having a plurality of cylinders. Since there are individual differences among the characteristics of the fuel injection valves that supply fuel to the respective cylinders, it will be difficult, in some cases, to make the fuel injection quantities precisely equal to each other among the cylinders. In addition, since the length and shape of the intake manifold are not the same among the cylinders, the intake air quantity may vary among the cylinders in some cases. In consequence, there will be a variation in the air-fuel ratio among the cylinders, which leads to differences in the $H_2$ concentration in the exhaust gas among the cylinders.

Here, the magnitude of the variation of the air-fuel ratio among the cylinders will be referred to as the "degree of air-fuel ratio variation among cylinders". If the degree of air-fuel ratio variation among cylinders becomes unduly large, deterioration of exhaust emissions will result, or fluctuations in the torque will be caused due to differences in the generated torque among the cylinders.

In view of the above, the control apparatus for an internal combustion engine according to the present invention may be characterized by comprising an air-fuel ratio sensor provided in an exhaust passage of a multi-cylinder internal combustion engine, an exhaust air-fuel ratio detection unit for detecting the air-fuel ratio of the exhaust gas discharged from said multi-cylinder internal combustion engine based on the output signal output by said sensor element, and an estimation unit for obtaining the width of variation of said air-fuel ratio during a specific sampling time and estimating the degree of air-fuel ratio variation among cylinders based on the width of variation.

With the above-described configuration, the air-fuel ratio of the exhaust gas discharged from the multi-cylinder internal combustion engine is detected based on the output signal output by the sensor element. If the degree of air-fuel ratio variation among cylinders is high, the variation in the $H_2$ concentration in the exhaust gases discharged from the respective cylinders becomes large, and consequently the value of the detected air-fuel ratio will fluctuate. According to the present invention, the width of variation in the air-fuel ratio during the specific sampling time is obtained. The width of variation may be defined as the absolute value of the difference between the maximum value and the minimum value of the air-fuel ratio detected during the specific sampling time. Alternatively, the width of variation may be defined as the maximum absolute value of the difference between the detected value of the air-fuel ratio and a target air-fuel ratio during the specific sampling time.

The specific sampling time refers to a period over which the detected value of the air-fuel ratio is monitored in order to obtain the aforementioned width of variation, and the specific sampling time may be determined in advance by experiments. The degree of air-fuel ratio variation among cylinders is estimated based on the width of variation in the air-fuel ratio thus obtained. In the present invention, the larger the aforementioned width of variation is, the higher the estimated value of the degree of air-fuel ratio variation is. Thus, the degree of air-fuel ratio variation among cylinders can be estimated excellently.

According to the present invention, if the estimated degree of air-fuel ratio variation among cylinders exceeds a specific value, it may be concluded that the degree of air-fuel ratio variation falls in a specific excessively large variation region. The specific excessively large variation region is a region in which the degree of air-fuel ratio variation among cylinders is considered to be so high that deterioration of exhaust emissions and/or fluctuations in the torque of the internal combustion engine can be caused.

Here, the width of variation corresponding to the degree of air-fuel ratio variation among cylinders just equal to the aforementioned specific value will be referred to as the specific variation width. Then, if the width of variation exceeds the specific variation width, it is concluded that the degree of air-fuel ratio variation among cylinders falls in the specific excessively large variation region. If this occurs, it is preferred that the driver be notified of the fact that the degree of air-fuel ratio variation among cylinders is high, by a warning unit such as tuning on a warning lamp.

Advantageous Effect of the Invention

The present invention can provide an air-fuel ratio sensor with which an improvement in the accuracy in detecting the air-fuel ratio of detection target gas and an improvement in the response characteristics can both be achieved.

DESCRIPTION OF THE REFERENCE SIGNS

Figure 1:
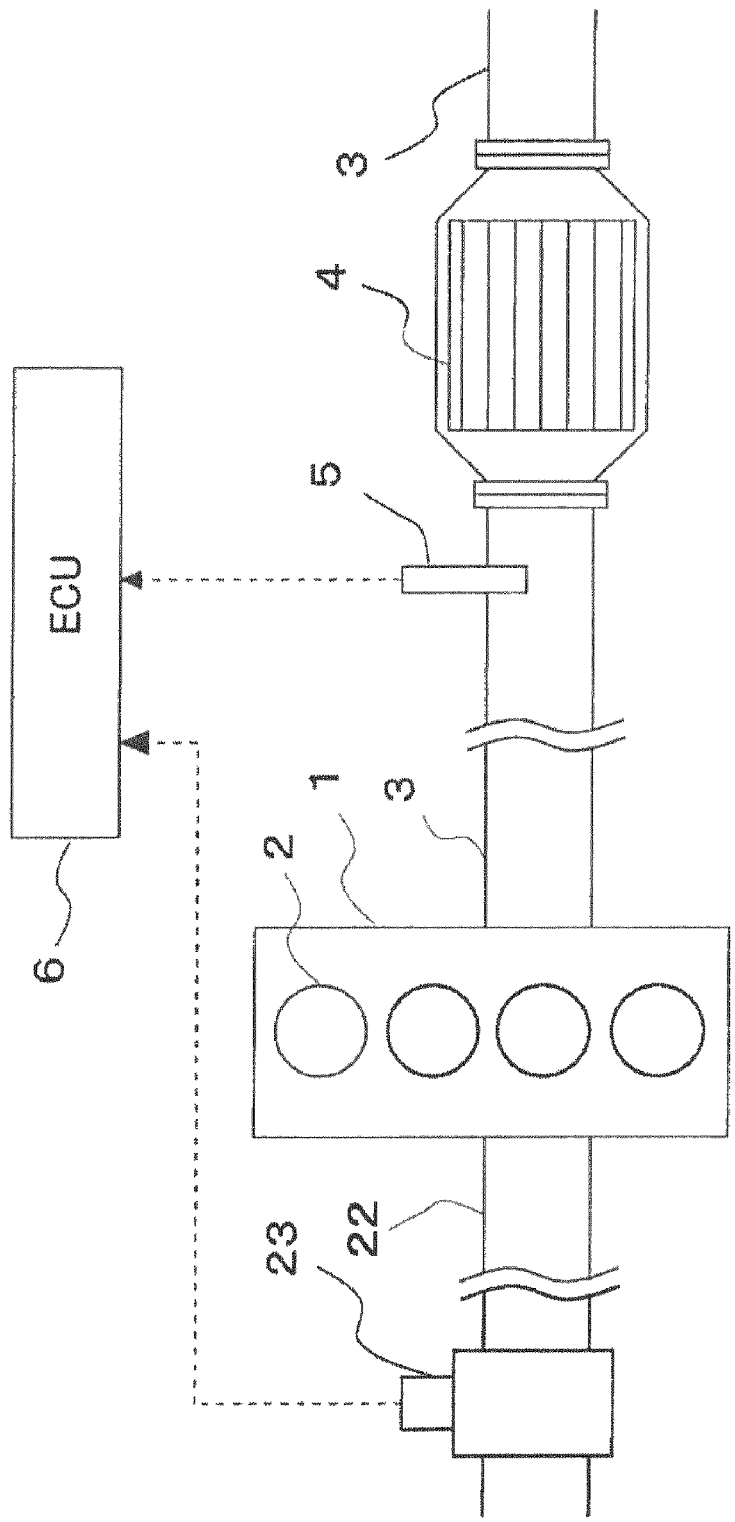
FIG. 1 is a diagram showing the general configuration of an internal combustion engine to which an air-fuel ratio sensor according to embodiment 1 is applied and its air-intake and exhaust system.

1: internal combustion engine
2: cylinder
3: exhaust pipe
4: three-way catalyst
5: air-fuel ratio sensor
6: ECU
8: protection cover
9: vent hole
10: sensor main unit
11: sensor element
12: exhaust side electrode
13: atmosphere side electrode
14: heater layer
16: atmosphere chamber
18: diffusion-controlling layer
19: mask layer
20: catalyst layer

THE BEST MODE FOR CARRYING OUT THE INVENTION

In the following, the best mode for carrying out the present invention will be described in detail by way of example. The dimensions, materials, shapes and relative arrangements etc. of the components that will be described in connection with this embodiment are not intended to limit the technical scope of the present invention only to them, unless particularly specified.

Embodiment 1

FIG. 1 is a diagram showing the general configuration of an internal combustion engine to which an air-fuel ratio sensor according to this embodiment is applied and the air-intake and exhaust system thereof. The internal combustion engine 1 shown in FIG. 1 is a gasoline engine having four cylinders 2.

The internal combustion engine 1 is connected with an intake pipe 22 and an exhaust pipe 3. An air flow meter 23 that outputs an electrical signal indicative of the quantity of intake air flowing in the intake pipe 22 is provided in the middle of the intake pipe 22. The air flow meter 23 is electrically connected with an ECU 6 that will be described later, and an output signal from the air flow meter 23 is input to the ECU 6, whereby the intake air quantity is detected.

A three-way catalyst 4 that purifies the exhaust gas discharged from the internal combustion engine 1 is provided in the middle of the exhaust pipe 3. The tree-way catalyst 4 is adapted to be able to purify the exhaust gas by oxidizing carbon monoxide (CO) and hydrocarbon (HC) discharged from the internal combustion engine 1 and reducing nitrogen oxides (NOx). An air-fuel ratio sensor 5 that detects the air-fuel ratio of the exhaust gas flowing into the three-way catalyst 4 is provided in the exhaust pipe 3 upstream of the three-way catalyst 4. The details of the air-fuel ratio sensor 5 will be described later. The exhaust pipe 3 is connected to a muffler that is not shown in the drawings at a position downstream of the three-way catalyst 4.

An electronic control unit (ECU) 6 that controls the internal combustion engine and its exhaust system is annexed to the internal combustion engine. The ECU 6 controls the operation state of the engine 1 according to the operation conditions of the internal combustion engine 1 and requests made by the driver. For example, the ECU 6 determines the air-fuel ratio of the exhaust gas based on the output signal of the air-fuel ratio sensor 5, and controls the quantity of fuel injected through the fuel injection valve (not shown) by feedback to make the air-fuel ratio equal to a target air-fuel ratio (e.g. the theoretical air-fuel ratio). In this embodiment, the exhaust gas corresponds to the detection target gas.

Figure 2:
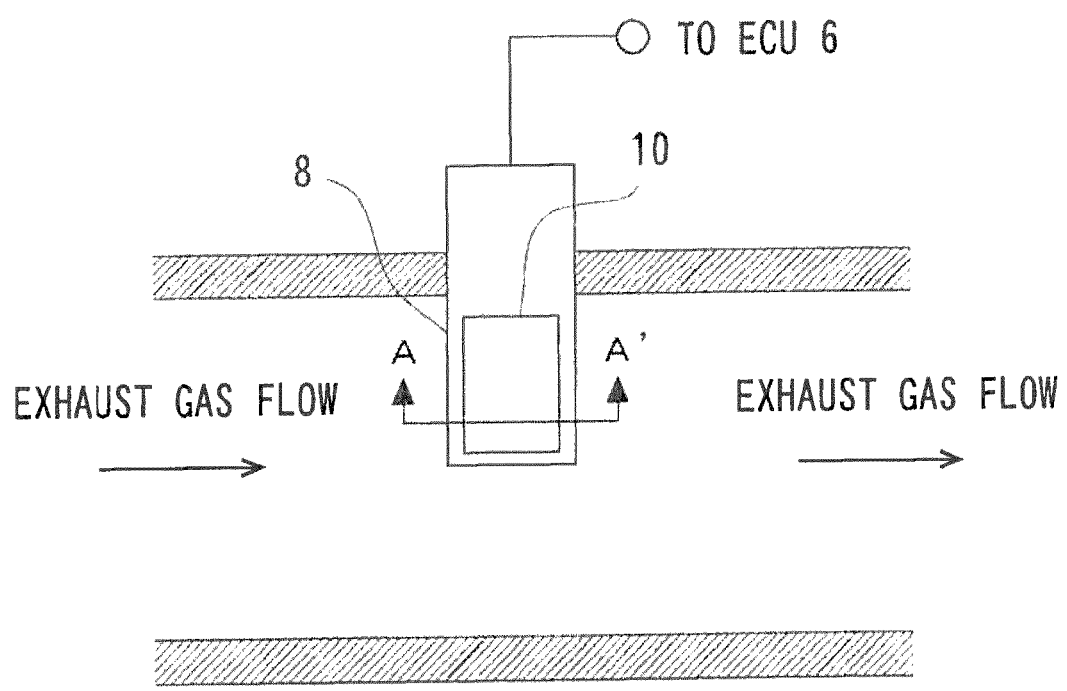
FIG. 2 is a schematic enlarged cross sectional view of a portion around an air-fuel ratio sensor shown in FIG. 1.
Figure 3:
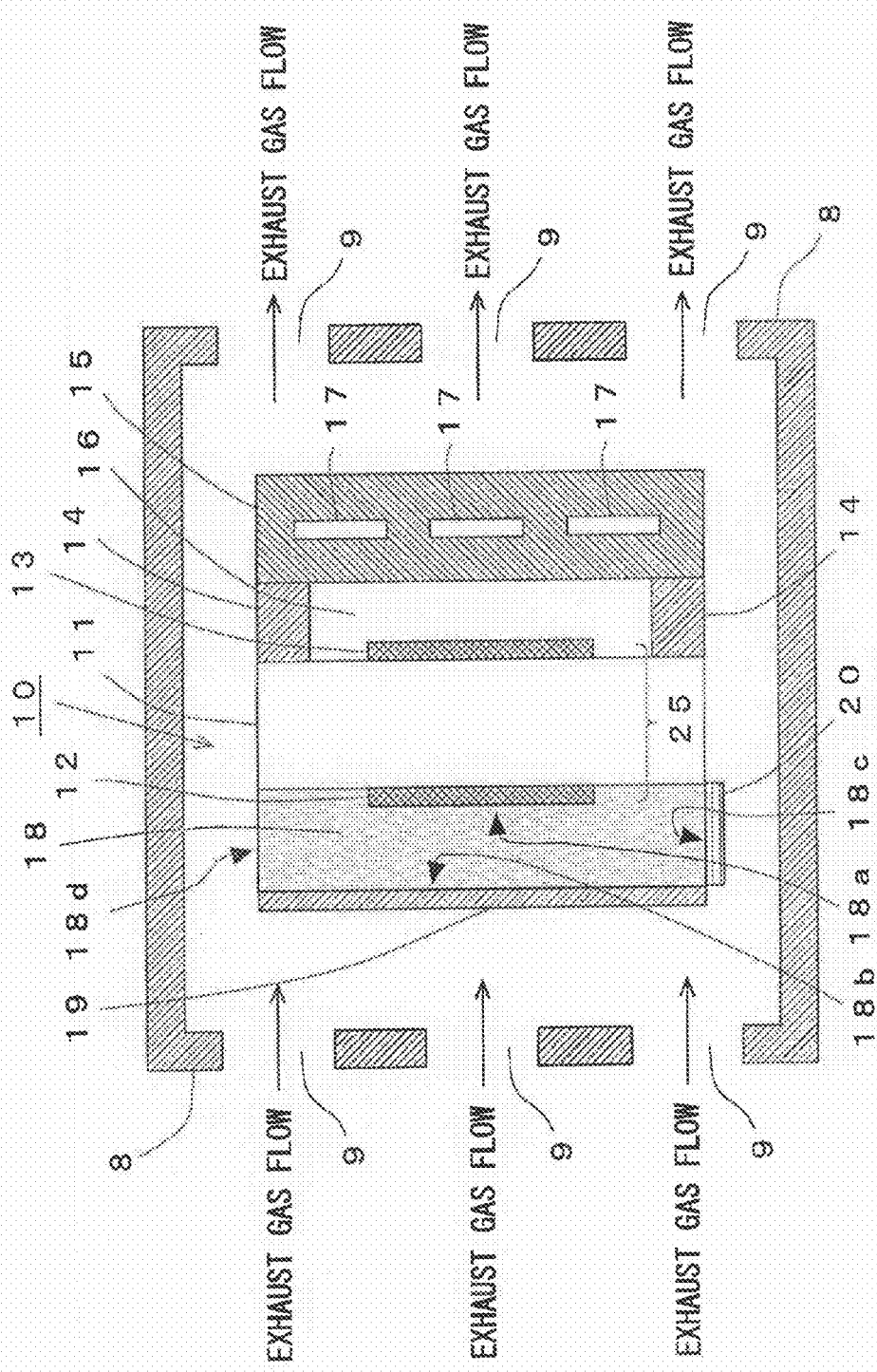
FIG. 3 is a cross sectional view taken along line A-A' in FIG. 2.

Next, the detailed construction of the air-fuel ratio sensor 5 will be described with reference to FIGS. 2 and 3. FIG. 2 is an enlarged schematic cross sectional view of the portion around the air-fuel ratio sensor 5 shown in FIG. 1. FIG. 3 is a cross sectional view taken along line A-A' in FIG. 2. In FIG. 2, the portions same as those in FIG. 1 are denoted by the same reference numerals, and descriptions thereof will be omitted.

In FIG. 2, the air-fuel ratio sensor 5 comprises a sensor main unit 10 that will be described later and a protection cover 8 or a heat-resistant housing member that houses the sensor main unit 10, a portion of the protection cover 8 being exposed to the interior of the exhaust pipe 3. The mechanical strength of the sensor main unit 10 is ensured by the protection cover 8 in which it is housed.

As shown in FIG. 3, the protection cover 8 has a plurality of vent holes 9 provided on its surface, which allow communication between the interior and the exterior of the protection cover 8. Thus, the air-fuel ratio sensor 5 is constructed in such a way that the exhaust gas flowing in the exhaust pipe 3 can reach the sensor main unit 10 through the vent holes 9 of the protection cover 8.

Next, the general configuration of the sensor main unit 10 will be described. The sensor main unit 10 is a laminated sensor in which components that will be described in the following are laminated together. The sensor main unit 10 has a sensor element 11 made of an oxygen ion conductive solid electrolyte. The sensor element 11 is made, for example, of zirconium oxide (zirconia) and has a plate-like shape as illustrated. On portions of two surfaces of the sensor element 11 are provided an exhaust side electrode 12 and the atmosphere side electrode 13 that are made of a metal material having high catalyst activity, such as platinum. As the exhaust side electrode 12 is provided on one surface of the sensor element 11 and the atmosphere side electrode 13 is provided on the other surface of the sensor element 11, the sensor element 11 is sandwiched between the two electrodes. In this embodiment, the exhaust side electrode 12 and the atmosphere side electrode 13 correspond to the detection target gas side electrode and the atmosphere side electrode according to the present invention.

An atmosphere chamber 16 enclosed by a spacer member 14 and a heater layer 15 is formed on the other surface of the sensor element 11. The atmosphere chamber 16 is in communication with the atmosphere via an atmosphere hole that is not shown in the drawings, so that the atmosphere side electrode 13 is kept exposed to the atmosphere even through the air-fuel ratio sensor 5 is disposed in the exhaust pipe 3.

Heaters 17 are embedded in the heater layer 15. The air-fuel ratio sensor 5 provides the sensor function of sensing or detecting the air-fuel ratio of the exhaust gas when it reaches a certain active temperature. The heaters 17 can heat the sensor main unit 10 to a desired active temperature (e.g. 700° C.) with supply of electric power from an external electrical circuit (not shown). The electrical circuit is electrically connected with the ECU 6, and the electric power supplied to the heaters 17 is controlled by the ECU 6.

A diffusion-controlling layer 18 is laminated on the one surface of the sensor element 11 to cover the entire area of the one surface of the sensor element 11 and the exhaust side electrode 12. The diffusion-controlling layer 18 is a member made of a porous material such as a ceramic and has the function of controlling or limiting the diffusion of the exhaust gas. Specifically, the diffusion-controlling layer 18 is porous but dense to the extent that various components in the exhaust gas can diffuse at an appropriate diffusion rate. The diffusion-controlling layer 18 is produced in such a way that it has substantially homogeneous characteristics in regard to the pore diameter and density. The outer shape of the diffusion-controlling layer 18 is substantially the same as the sensor element 11 except for the shape with respect to the thickness direction.

Here, among the surfaces of the diffusion-controlling layer 18, the surface with which the one surface of the sensor element 11 is covered will be referred to as the "covering surface" 18a, and the surface opposite to the covering surface 18a will be referred to as the "opposite-to-covering surface" 18b. The opposite-to-covering surface 18b of the diffusion-controlling layer 18 is covered with a mask layer 19. The mask layer 19 is a dense member made of alumina or the like, and the exhaust gas cannot pass through the mask layer 19. Consequently, the infiltration of the exhaust gas into the diffusion-controlling layer 18 through the portion on which the mask layer 19 is provided is restricted.

A catalyst layer 20 is provided on one surface (18c) of a pair of opposed side surfaces (denoted by 18c and 18d in the drawing) among the four faces other than the covering surface 18a and the opposite-to-covering surface 18b among the six surfaces of the diffusion-controlling layer 18, while the other surface (18d) is exposed (namely, no catalyst layer 20 is provided on the other surface 18d). The catalyst layer 20 is composed of a porous layer made of alumina or the like serving as a catalyst support, on which a catalyst component such as platinum or rhodium is supported, and has the function of promoting oxidation of the hydrogen ($H_2$) component.

Here, the surface 18c on which the catalyst layer 20 is provided will be referred to as the "surface with catalyst layer", and the surface 18d on which no catalyst layer 20 is provided will be referred to as the "surface without catalyst layer". Furthermore, mask layer 19 as described above are provided on the pair of opposed side surfaces of the diffusion-controlling layer 18 perpendicular to the surface with catalyst layer 18c and the surface without catalyst layer 18d. With the above-described construction of the sensor main unit 10, infiltration and diffusion of the exhaust gas into the diffusion-controlling layer 18 through the surfaces on which the mask layers 19 are provided are restricted. Therefore, the exhaust gas flows into the diffusion-controlling layer 18 through the surface with catalyst layer 18c and the surface without catalyst layer 18d and diffuses in the diffusion-controlling layer 18. In this embodiment, the surface with catalyst layer 18c and the surface without catalyst layer 18d correspond the entrance portion according to the present invention.

Here, a description will be made of the principle of detecting or determining the air-fuel ratio of the exhaust gas by the air-fuel ratio sensor 5. The exhaust gas introduced into the interior of the protection cover 8 through vent holes 9 flows into the diffusion-controlling layer 18 through the surface with catalyst layer 18c and the surface without catalyst layer 18d and travels toward the exhaust side electrode 12 while diffusing in the interior of the diffusion-controlling layer. The exhaust gas contains reducing agents such as CO, $H_2$, and HC and oxidizing agents such as $O_2$ and NOx. These components react with each other while they travel to the surface of the exhaust side electrode 12 and after reaching the exhaust side electrode 12, until an equilibrium is reached. In the case where the air-fuel ratio of the exhaust gas is equal to a theoretical air-fuel ratio (or stoichiometric air-fuel ratio), the oxidizing agents and the reducing agents both disappear. On the other hand, in the case where the air-fuel ratio is rich, the reducing agents will remain, and in the case where the air-fuel ratio is lean, the oxidizing agents will remain.

Here, the portion composed of the exhaust side electrode 12, the atmosphere side electrode 13, and the sensor element 11 sandwiched between them will be referred to as the "cell 25". In this embodiment, a certain application voltage is applied between the exhaust side electrode 12 and the atmosphere side electrode 13 by a power supply line that is not shown in the drawings. In the state in which the application voltage is applied between the electrodes, in the case where there remain oxidizing agents in the exhaust gas that has come to the surface of the exhaust side electrode 12, $O_2$ is pumped from the exhaust side electrode 12 toward the atmosphere side electrode 13, whereby a sensor current flows in the cell 25. On the other hand, in the case where there remain reducing agents around the exhaust side electrode 12, $O_2$ that is needed to vanish the reducing agents is pumped from the atmosphere side electrode 13 toward the exhaust side electrode 12, whereby a sensor current flows in the cell 25.

As the diffusion rate of the exhaust gas is limited by the diffusion-controlling layer 18, there is a region in which the sensor current value saturates at a constant value in spite of increases in the application voltage, and the sensor current value at that time shows a characteristic proportional to the air-fuel ratio of the exhaust gas. This sensor current value is generally referred to as the "limit current value" in some cases. By sensing this sensor current value, the ratio of the oxidizing agents and the reducing agents on the surface of the exhaust side electrode 12 can be determined, namely the air-fuel ratio of the exhaust gas can be determined.

Specifically, the air-fuel ratio sensor 5 is provided with a sensor current value detection circuit (not shown) that generates an output indicative of the sensor current value. The output from the sensor current value detection circuit is input to an A/D converter (not shown) provided in the ECU 6, and the ECU 6 determines the air-fuel ratio of the exhaust gas by A/D-converting the input value. The ECU 6 can smooth the output value from the sensor current value detection circuit in the air-fuel ratio sensor 5 by performing a smoothing process.

The exhaust gas discharged from the internal combustion engine 1 contains $H_2$. $H_2$ has, characteristically, a higher diffusion rate as compared to the other components in the gas, in particular $O_2$. Therefore, in the case where $H_2$ is contained in the exhaust gas diffusing in the diffusion-controlling layer 18, a larger amount of $H_2$, which has a higher diffusion rate, reaches the exhaust side electrode 12 as compared to $O_2$.

In other words, the ratio of $H_2$ and $O_2$ in the exhaust gas is higher at the time when the exhaust gas reaches the exhaust side electrode 12 than at the time when the exhaust gas enters the diffusion-controlling layer 18. Since $H_2$ is reducing agent, the sensor current value generated in the cell 25 can be detected as a value shifted to richer air-fuel ratios as compared to the air-fuel ratio of the exhaust gas around the air-fuel ratio sensor 5. The amount of the shift to richer air-fuel ratios tends to increase as the $H_2$ concentration in the exhaust gas increases.

Figure 4:
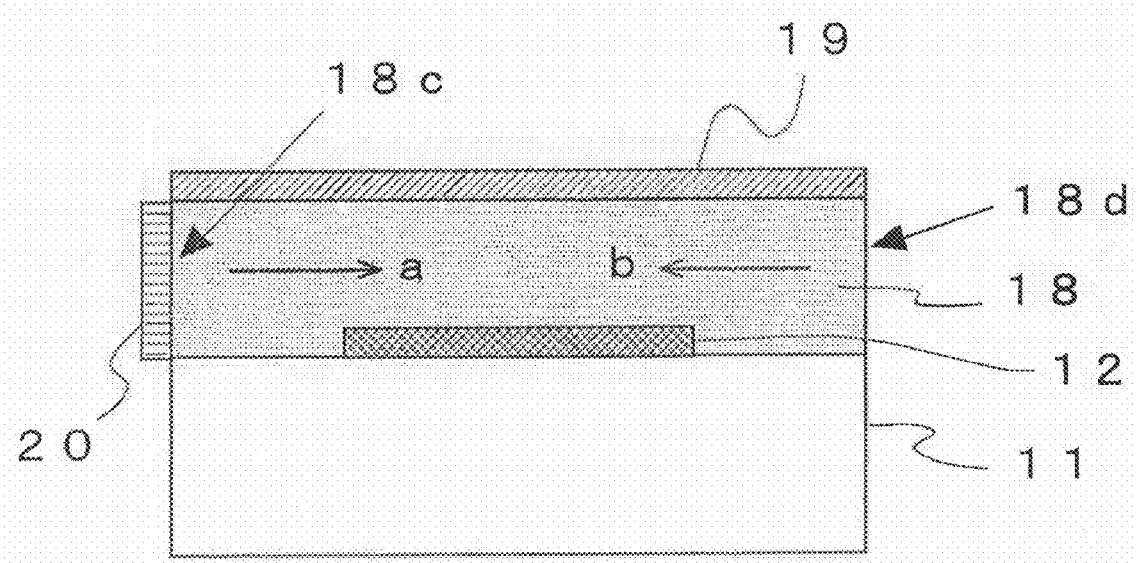
FIG. 4 is a schematic diagram showing a portion around a diffusion-controlling layer and an exhaust side electrode of the air-fuel ratio sensor.

Next, accuracy of air-fuel ratio detection by the air-fuel ratio sensor 5 according to this embodiment and its response characteristics will be discussed in detail. FIG. 4 is a schematic diagram showing the diffusion-controlling layer 18, the exhaust side electrode 12, and relevant portions of the air-fuel ratio sensor 5. The exhaust gas flowing into the interior of the protection cover 8 from the exhaust pipe 3 enters the diffusion-controlling layer 18 through the surface with catalyst layer 18c on which the catalyst layer 20 is provided and the surface without catalyst layer 18d on which no catalyst layer 20 is provided, and diffuses toward the exhaust side electrode 12.

The direction of diffusion of the exhaust gas flowing into the diffusion-controlling layer 18 through the surface with catalyst layer 18c is represented by arrow a, and such gas will be referred to as the "catalyst layer inflowing gas". On the other hand, the direction of diffusion of the exhaust gas flowing into the diffusion-controlling layer 18 through the surface without catalyst layer 18d is represented by arrow b, and such gas will be referred to as the "non-catalyst layer inflowing gas". The exhaust gas that has flowing into the interior of the protection cover 8 through the vent holes 9 and has not reached yet the surface without catalyst layer 18d or the surface of the catalyst layer 20 will be referred to as the "gas not having reached the sensor".

In order for the gas not having reached the sensor to flow into the diffusion-controlling layer 18 through the surface with catalyst layer 18c, it necessarily passes through the catalyst layer 20. Consequently, $H_2$ contained in this exhaust gas is, for the most part, oxidized as the exhaust gas passes through the catalyst layer 20. Therefore, the catalyst layer inflowing gas diffuses in the direction of arrow a in the drawing in an equilibrium gas state. In this connection, since the air-fuel ratio of the exhaust gas does not change through the equilibrium reaction of $H_2$ in the catalyst layer 20, and the $H_2$ component does not exist any more in the process of diffusion of the catalyst layer inflowing gas in the diffusion-controlling layer 18, the balance of the oxidizing agents and the reducing agents hardly changes. In consequence, the gas that reaches the surface of the exhaust side electrode 20 has an air-fuel ratio substantially equal to the air-fuel ratio of the gas not having reached the sensor that has not reached the catalyst layer 20. Consequently, the accuracy of detection of air-fuel ratio by the air-fuel ratio sensor 5 is ensured.

The performance of the air-fuel ratio sensor 5 is desired to be improved in terms of response characteristics as well as accuracy of detection of the air-fuel ratio. Since the catalyst layer inflowing gas diffuses in the diffusion-controlling layer 18 after it has been used in the catalytic reaction in the catalyst layer 20, the time of arrival of the catalyst layer inflowing gas to the exhaust side electrode 12 delays a little. On the other hand, in the air-fuel ratio sensor 5 according to this embodiment, the non-catalyst layer inflowing gas can be delivered to the exhaust side electrode 12 through the surface without catalyst layer 18d without passing through the catalyst layer 20. In this embodiment, the catalyst layer inflowing gas that enables high accuracy in the air-fuel ratio detection and non-catalyst layer inflowing gas that enables high response speed merge together around the exhaust side electrode 12, whereby the accuracy of detection of the air-fuel ratio can be enhanced, and in addition good response characteristics can be maintained.

In this embodiment, the non-catalyst layer inflowing gas contains $H_2$. Therefore, if attention is focused only on the accuracy of air-fuel ratio detection, this sensor may be considered to be inferior in detection accuracy to air-fuel ratio sensors in which the catalyst layer 20 is formed also on the surface without catalyst layer 18d in addition to the surface with catalyst layer 18c, or air-fuel ratio sensors in which entire exhaust gas flowing into the diffusion-controlling layer 18 is caused to pass through the catalyst layer 20. However, such sensors suffer, in contrast, from deterioration in the response characteristics in air-fuel ratio detection. In the air-fuel ratio sensor 5 according to this embodiment, improvement in the accuracy of air-fuel ratio detection and improvement in the response characteristics are both achieved, whereby overall performance as an air-fuel ratio sensor can be improved. In addition, a reduction in the manufacturing cost of the air-fuel ratio sensor 5 can be achieved, because no catalyst layer 20 is provided on the surface without catalyst layer 18d.

Various changes may be made to the area over which the catalyst layer 20 provided on the side surface of the diffusion-controlling layer 18 extends without departing from the essential scope of the present invention. Specifically, any mode in which exhaust gas having passed through the catalyst layer and exhaust gas not having passed through the catalyst layer can diffuse in the diffusion-controlling layer 18 is acceptable.

Figure 5:
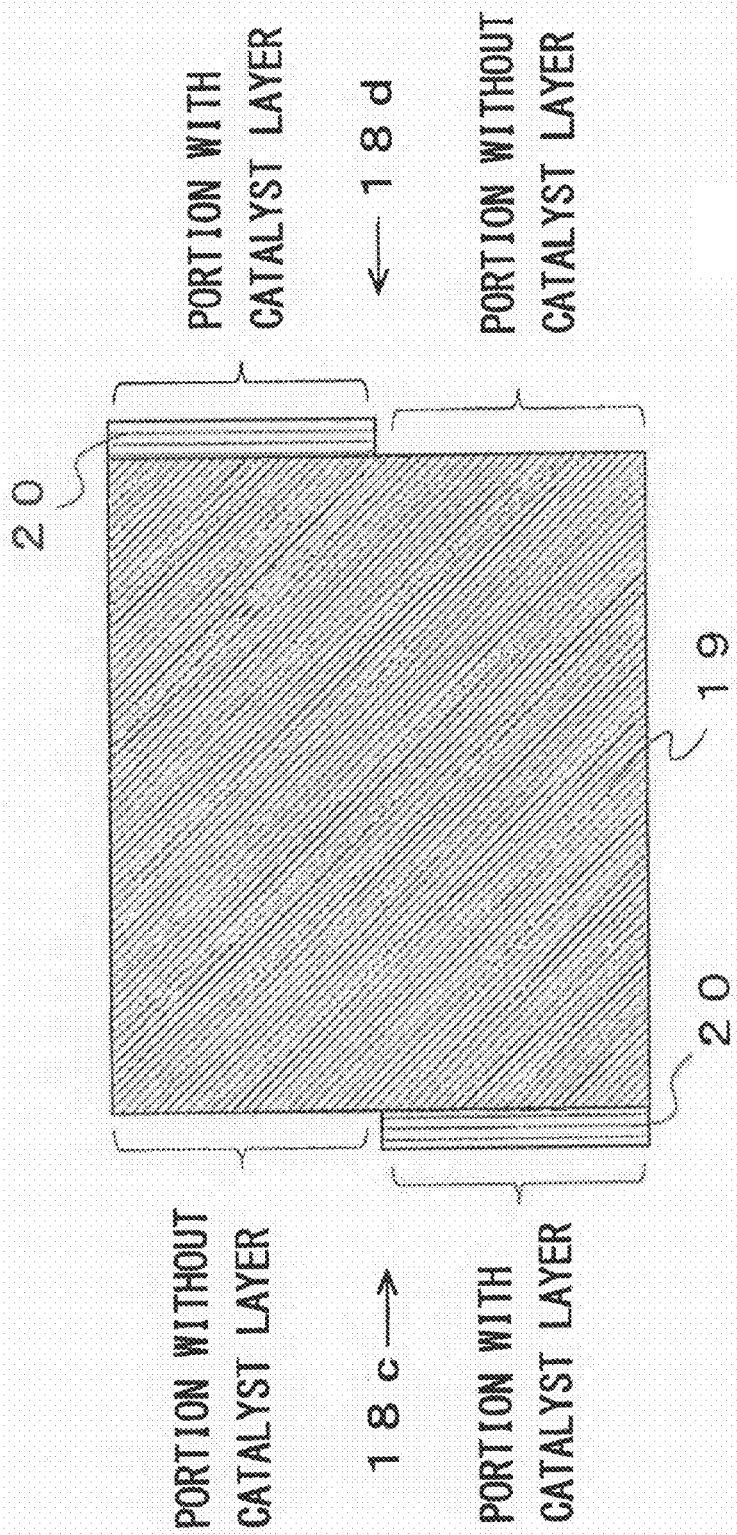
FIG. 5 is a diagram showing a modification of the pattern of catalyst layer provided on the diffusion-controlling layer.

FIG. 5 is a diagram showing a modification of the pattern of the catalyst layer 20 provided on the diffusion-controlling layer 18. FIG. 5 shows the sensor main unit 11 as seen from the side of the mask layer 19 with which the opposite-to-covering surface 18b of the diffusion-controlling layer 18 is covered. As shown in the drawing, the surfaces 18c and 18d of the diffusion-controlling layer 18 may include a portion with catalyst layer on which the catalyst layer 20 is provided and a portion without catalyst layer. The area of the portion with catalyst layer and the area of the portion without catalyst layer may be equal to or different from each other. In other words, the ratio of the area of the portion with catalyst layer and the area of the portion without catalyst layer (which ratio will be hereinafter referred to as the "catalyst layer ratio") may be changed fitly. It is preferred that the catalyst layer ratio be changed in accordance with the balance between the degree of accuracy of air-fuel ratio detection that the air-fuel ratio sensor 5 is required to provide and the response performance thereof. More specifically, if the accuracy of detection of the air-fuel ratio is to be enhanced, the catalyst layer ratio may be increased, and if the response performance is to be enhanced, the catalyst layer ratio may be decreased.

The temperature of the catalyst layer 20 provided on the surface with catalyst layer 18c can be high due to the heat of the exhaust gas and application of heat by the heater 17. If sintering or heat deterioration occurs in the catalyst layer 20 consequently, the accuracy of detection of the air-fuel ratio may be deteriorated in some cases. In this embodiment, deterioration of the accuracy of detection of the air-fuel ratio caused by deterioration of the catalyst layer 20 can be reduced by making the quantity of catalyst supported on unit area of the surface with catalyst layer 18c (which may be the quantity of catalyst applied on unit area and will be referred to as the "unit support quantity" hereinafter) sufficiently large.

It is considered that the larger the unit support quantity of the catalyst layer 20 is, the longer the time taken by reaction of $H_2$ in the exhaust gas is. In the case of the air-fuel ratio sensor 5 according to this embodiment, good response characteristics in the detection of the air-fuel ratio can be ensured by the presence of the non-catalyst layer inflowing gas that diffuses in the diffusion-controlling layer 18 without passing through the catalyst layer 20. In addition, since the cost can be reduced because the catalyst layer 20 is not provided on the surface without catalyst layer 18d, an increase in the unit support quantity of the catalyst layer 20 on the surface with catalyst layer 18c does not lead to an increase in the total cost in comparison with the air-fuel ratio sensors of the type in which the entire exhaust gas flowing into the diffusion-controlling layer 18 is cased to pass through the catalyst layer 20.

The term "air-fuel ratio sensor 5" in this embodiment collectively denotes a unit that can output a physical quantity indicative of the oxygen concentration in the detection target gas to detect or measure the air-fuel ratio in the internal combustion engine 1, and the air-fuel ratio sensor 5 may be, for example, a linear air-fuel ratio sensor, an $O_2$ sensor, or the like. The physical quantity indicative of the oxygen concentration may be a current value or a voltage value. Although the detection target gas in this embodiment is the exhaust gas of the internal combustion engine 1, the detection target gas is not limited to this. The detection target gas may be, for example, the intake air of the internal combustion engine 1.

Embodiment 2

A mode different from embodiment 1 will be described as an embodiment for carrying out the present invention. The general configuration of the air-fuel ratio sensor 5 according to this embodiment and the internal combustion engine 1 to which the air-fuel ratio sensor 5 is applied is the same as that of embodiment 1, and description thereof will be omitted.

In the internal combustion engine 1 according to this embodiment, a fuel injection quantity with which a target air-fuel ratio is achieved can be calculated based on the intake air quantity measured by the air flow meter 23. Furthermore, the air-fuel ratio can be feedback-controlled by adjusting the fuel injection quantity based on the air-fuel ratio detected by the air-fuel ratio sensor 5.

By this control, the air-fuel ratio of the entire internal combustion engine 1 (which will be hereinafter referred to as the "entire air-fuel ratio") can be controlled precisely. When the entire air-fuel ratio is to be controlled, it is generally controlled in such a way that it becomes equal to the theoretical air-fuel ratio (stoichiometric air-fuel ratio) so that the exhaust gas purifying effect of the three-way catalyst 4 works excellently. In the following description, it is assumed that the ECU 6 controls the internal combustion engine so that the entire air-fuel ratio becomes equal to the theoretical air-fuel ratio.

However, in the internal combustion engine 1 having four cylinders 2 (i.e. number one cylinder #1 to number four cylinder #4), generally, the length and shape of the intake manifold (not shown) connected to the intake pipe 22 are not the same among the cylinders, and consequently it is difficult to make the intake air quantities precisely equal to each other among the cylinders. In addition, since there are individual differences among the characteristics of the fuel injection valves (not shown) that supply fuel to the respective cylinders 2, it is also difficult to make the fuel injection quantities precisely equal to each other among the cylinders. In consequence, there is a variation in the air-fuel ratio among the cylinders, which leads to differences in the $H_2$ concentration in the exhaust gas among the cylinders. For this reason, even if the entire air-fuel ratio is regulated to the theoretical air-fuel ratio, there usually is a variation in the value of the air-fuel ratio detected by the air-fuel ratio sensor 5.

Here, the magnitude of the variation of the air-fuel ratio among the cylinders will be referred to as the "degree of air-fuel ratio variation among cylinders". If the degree of air-fuel ratio variation among cylinders becomes unduly large, deterioration of exhaust emissions will result, or fluctuations in the torque will be caused due to differences in the generated torque among the cylinders. In view of this, in this embodiment, the ECU 6 estimates the degree of air-fuel ratio variation among cylinders, and if it is determined that the estimated value falls in an excessively large variation region, a warning lamp (not shown) is turned on to give a caution to the driver. The excessively large variation region is a region in which the degree of air-fuel ratio variation among cylinders is considered to be so high that deterioration of exhaust emissions and/or fluctuations in the torque of the internal combustion engine can be caused.

As described above, when the degree of air-fuel ratio variation among cylinders is high, the variation in the $H_2$ concentration in the exhaust gas discharged from the cylinders 2 also becomes larger. Consequently, the fluctuation in the raw output value (i.e. the output value to which smoothing process has not been applied) input from the air-fuel ratio sensor 5 to the ECU 6 becomes larger even if the entire air-fuel ratio is the same. In view of this, in this embodiment, the raw output value of the air-fuel ratio is monitored over a standard sampling period $\Delta tbs$, and the air fuel ratio variation width $\Delta AF$ representing the width or magnitude of variation in the raw output value is obtained.

The air-fuel ratio variation width $\Delta AF$ in the context of this embodiment is defined as the absolute value of the difference between the maximum value and the minimum value among the raw output values of the air-fuel ratio detected during the standard sampling period $\Delta tbs$. Alternatively, the air-fuel ratio variation width $\Delta AF$ may be defined as the maximum absolute value of the difference between the raw output value of the air-fuel ratio detected during the standard sampling period $\Delta tbs$ and the target air-fuel ratio. In this embodiment, the air-fuel ratio variation width $\Delta AF$ corresponds to the width of variation in the air-fuel ratio according to the present invention.

Figure 6:
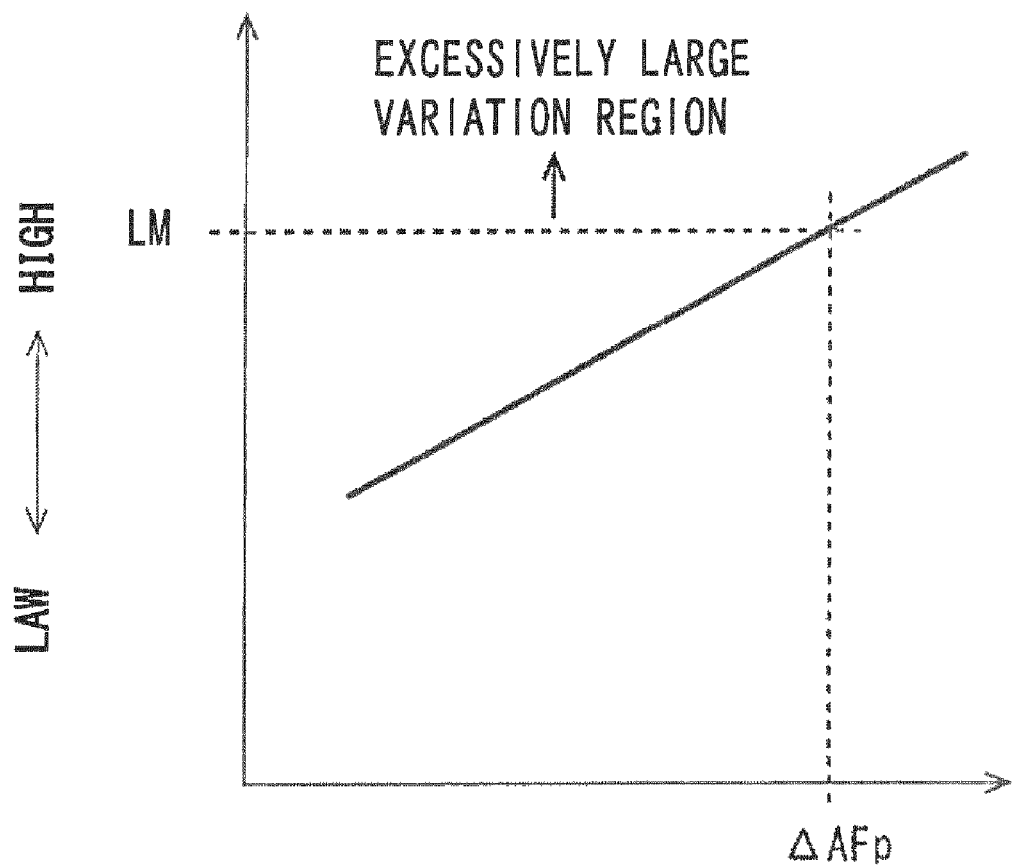
FIG. 6 shows a map in which relationship between the width of variation in the air-fuel ratio $\Delta AF$ and the degree of air-fuel ratio variation among cylinders is stored.

In this embodiment, the degree of air-fuel ratio variation among cylinders is estimated by substituting the air-fuel ratio variation width $\Delta AF$ into a map in which relationship between the air-fuel ratio variation width $\Delta AF$ and the degree of air-fuel ratio variation among cylinders is stored as shown in FIG. 6. As shown in FIG. 6, the larger the air-fuel ratio variation width $\Delta AF$ is, the higher the estimated value of the degree of air-fuel ratio variation among cylinders will be. If the degree of air-fuel ratio variation among cylinders exceeds a specific value LM, it is concluded that the degree of air-fuel ratio variation falls in the excessively large variation region.

Here, the value of the air-fuel ratio variation width $\Delta AF$ corresponding to the degree of air-fuel ratio variation among cylinders just equal to the specific value LM will be referred to as the specific variation width $\Delta AFp$. Then, if the air-fuel ratio variation width $\Delta AF$ exceeds the specific variation width $\Delta AFp$, it is concluded that the degree of air-fuel ratio variation among cylinders falls in the excessively large variation region. Thus, the specific variation width $\Delta AFp$ serves as the upper limit of allowable values of the air-fuel ratio variation width $\Delta AF$ in suppressing deterioration of exhaust emissions and fluctuations of the torque of the internal combustion engine 1.

Although the relationship between the air-fuel ratio variation width $\Delta AF$ and the degree of variation in the air fuel ratio among cylinders shown in FIG. 6 is linear, they may have a correlation represented by a curve, as a matter of course.

Figure 7:
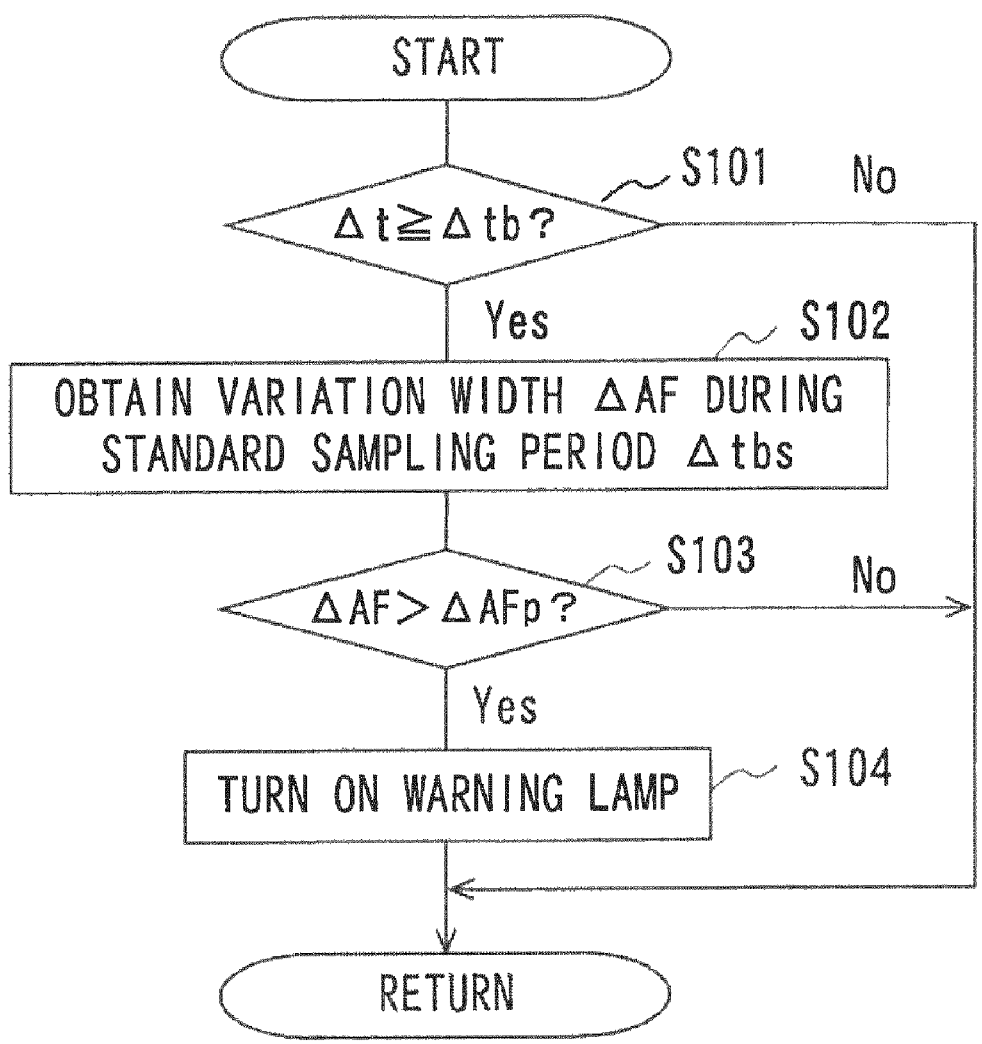
FIG. 7 is a flow chart of a control routine in embodiment 2.

In the following, a control executed by the ECU 6 will be described with reference to the flow chart of FIG. 7. FIG. 7 is a flow chart showing a control routine in this embodiment. This routine is a program stored in a ROM in the ECU 6, and executed at predetermined intervals during the operation of the internal combustion engine 1. In this embodiment, the ECU 6 that executes this routine corresponds to the exhaust air-fuel ratio detection unit and the estimation unit according to the present invention.

When this routine is executed, first in step S101, the time $\Delta t$ that has elapsed since the start-up of the internal combustion engine 1 is read by the ECU 6, and a determination is made as to whether or not the elapsed time $\Delta t$ is equal to or longer than a reference time $\Delta tb$. The reference time $\Delta tb$ may be a time required to warm up the internal combustion engine 1 or time required to heat the sensor main unit 10 to an active temperature by the heater 17 of the air-fuel ratio sensor 5 (i.e. the time required to warm up the air-fuel ratio sensor 5), which can be determined beforehand by experiments.

If the elapsed time $\Delta t$ is equal to or longer than the reference time $\Delta tb$ in this step, the process proceeds to step S102. On the other hand, if the elapsed time $\Delta t$ is shorter than the reference time $\Delta tb$, it is concluded that estimation of the degree of air-fuel ratio variation among cylinders should not be performed, and the routine is once terminated.

In step S102, the air-fuel ratio variation width $\Delta AF$ during the standard sampling period $\Delta tbs$ is obtained. Specifically, the raw output value of the air-fuel ratio sensor 5 is monitored over the reference sampling period $\Delta tbs$. Here, the raw output value refers, as described above, to the value obtained by A/D converting the output value of the sensor current detection circuit of the air-fuel ratio sensor 5 by the A/D converter provided in the ECU 6, and smoothing process has not been applied to it. The standard sampling period $\Delta tbs$ is a period over which the raw output value is monitored to obtain the width $\Delta AF$ of variation in the air-fuel ratio among the cylinders, and it may be determined in advance by experiments. In this embodiment, the standard sampling period $\Delta tbs$ corresponds to the specific sampling time according to the present invention.

In step S103, a determination is made as to whether or not the air-fuel ratio variation width $\Delta AF$ is larger than the specific variation width $\Delta AFp$. If an affirmative determination is made (namely, $\Delta AF > \Delta AFp$), it is concluded that the degree of air-fuel ratio variation among cylinders falls in the excessively large variation region, and the process proceeds to step S104. On the other hand, if a negative determination is made (namely, $\Delta AF \leq \Delta AFp$), it is concluded that the degree of air-fuel ratio variation among cylinders does not fall in the excessively large variation region, and the routine is once terminated. In step S104, the warning lamp is turned on to notify the driver that the degree of air-fuel ratio variation among cylinders is high. After completion of the process in this step, the routine is once terminated.

As described above, according to this control, since the degree of air-fuel ratio variation among cylinders is estimated based on the air-fuel ratio variation width $\Delta AF$ during the standard sampling period $\Delta tbs$, and a determination as to whether or not the degree of air-fuel ratio variation falls in the excessively large variation region can be made, no limitation is placed on the mounting position (location) of the air-fuel ratio sensor 5. Therefore, the air-fuel ratio sensor 5 can be disposed at a more downstream position in the exhaust pipe 3. Then, the air-fuel ratio sensor 5 can be prevented preferably from getting sprinkled with condensed water or splashing water that might be generated in particular during cold-start of the internal combustion engine 1. When this control is performed, the degree of air-fuel ratio variation among cylinders can be estimated in any operation state without any condition such as that the internal combustion engine 1 should be kept in a specific operation state.

The invention claimed is:

1. An air-fuel ratio sensor comprising:
   a sensor element that outputs an output signal indicative of the air-fuel ratio of a detection target gas;
   a pair of electrodes including a detection target gas side electrode to which said detection target gas is introduced and an atmosphere side electrode exposed to the atmosphere, which are arranged in such a way as to sandwich said sensor element;
   a diffusion-controlling layer that is disposed on said sensor element in such a way as to cover said detection target gas side electrode and introduces said detection target gas from an entrance portion through which said detection target gas flows in to said detection target gas side electrode; and
   a catalyst layer provided on a part of said entrance portion,
   wherein said entrance portion is provided on a pair of opposed side surfaces among four surfaces other than a covering surface that covers said detection target gas side electrode and an opposite-to-covering surface opposite to said covering surface among six surfaces that define said diffusion-controlling layer, and
   wherein said catalyst layer is provided on one of the pair of opposed surfaces on which said entrance portion is provided, and not provided on the other surface.

2. A control apparatus for an internal combustion engine comprising:
   an air-fuel ratio sensor as recited in claim 1, provided in an exhaust passage of a multi-cylinder internal combustion engine;
   an exhaust air-fuel ratio detection unit that detects the air-fuel ratio of exhaust gas discharged from said multi-cylinder internal combustion engine based on the output signal output by said sensor element; and
   an estimation unit that obtains the width of variation in said air-fuel ratio during a specific sampling time and estimating the degree of air-fuel ratio variation among cylinders based on said width of variation.

3. An air-fuel ratio sensor comprising:
   a sensor element that outputs an output signal indicative of the air-fuel ratio of a detection target gas;
   a pair of electrodes including a detection target gas side electrode to which said detection target gas is introduced and an atmosphere side electrode exposed to the atmosphere, which are arranged in such a way as to sandwich said sensor element;
   a diffusion-controlling layer that is disposed on said sensor element in such a way as to cover said detection target gas side electrode and introduces said detection target gas from an entrance portion through which said detection target gas flows in to said detection target gas side electrode; and
   a catalyst layer provided on a part of said entrance portion,
   wherein said entrance portion is provided on a pair of opposed side surfaces among four surfaces other than a covering surface that covers said detection target gas side electrode and an opposite-to-covering surface opposite to said covering surface among six surfaces that define said diffusion-controlling layer, and
   wherein a portion with catalyst layer on which the catalyst layer is provided and a portion without catalyst layer on which the catalyst layer is not provided are provided on each of the pair of opposed surfaces on which said entrance portion is provided.

4. A control apparatus for an internal combustion engine comprising:
   an air-fuel ratio sensor as recited in claim 3, provided in an exhaust passage of a multi-cylinder internal combustion engine;
   an exhaust air-fuel ratio detection unit that detects the air-fuel ratio of exhaust gas discharged from said multi-cylinder internal combustion engine based on the output signal output by said sensor element; and
   an estimation unit that obtains the width of variation in said air-fuel ratio during a specific sampling time and estimating the degree of air-fuel ratio variation among cylinders based on said width of variation.

* * * * *